United States Patent
Batthyány et al.

(10) Patent No.: US 11,400,066 B2
(45) Date of Patent: *Aug. 2, 2022

(54) METHODS OF TREATMENT OF INFLAMMATION RELATED CONDITIONS USING PLURIPOTENT ANTI-INFLAMMATORY AND METABOLIC MODULATORS

(71) Applicants: Institut Pasteur de Montevideo, Montevideo (UY); Universidad de la República, Montevideo (UY)

(72) Inventors: Carlos Batthyány, Montevideo (UY); Gloria Virginia López, Montevideo (UY); Carlos Escande, Montevideo (UY); Jorge Rodriguez Duarte, Ciudad de la Costa (UY); Williams Arturo Porcal Quinta, Montevideo (UY); Rosina Dapueto Capuccio, Montevideo (UY); Germán Adrian Galliussi López, Montevideo (UY); María Pia Garat Nuñez, Montevideo (UY)

(73) Assignees: INSTITUT PASTEUR DE MONTEVIDEO, Montevideo (UY); UNIVERSIDAD DE LA REPÚBLICA, Montevideo (UY)

( * ) Notice: Subject to any disclaimer, the term of this patent is extended or adjusted under 35 U.S.C. 154(b) by 0 days.

This patent is subject to a terminal disclaimer.

(21) Appl. No.: 16/746,035

(22) Filed: Jan. 17, 2020

(65) Prior Publication Data

US 2020/0147017 A1 May 14, 2020

Related U.S. Application Data

(63) Continuation of application No. 15/784,685, filed on Oct. 16, 2017, now Pat. No. 10,537,537.

(60) Provisional application No. 62/570,973, filed on Oct. 11, 2017, provisional application No. 62/408,458, filed on Oct. 14, 2016.

(51) Int. Cl.
*A61K 31/192* (2006.01)
*A61K 45/06* (2006.01)

(52) U.S. Cl.
CPC ............ *A61K 31/192* (2013.01); *A61K 45/06* (2013.01)

(58) Field of Classification Search
CPC .................................................. A61K 31/192
See application file for complete search history.

(56) References Cited

U.S. PATENT DOCUMENTS

| | | | |
|---|---|---|---|
| 10,537,537 B2 * | 1/2020 | Batthyany | ............... A61P 43/00 |
| 2006/0247263 A1 | 11/2006 | Siegmund | |
| 2018/0104202 A1 | 4/2018 | Batthyany et al. | |
| 2020/0147017 A1 | 5/2020 | Batthyány et al. | |

FOREIGN PATENT DOCUMENTS

| | | |
|---|---|---|
| JP | S48 34850 A | 5/1973 |
| WO | 2005037323 A1 | 4/2005 |
| WO | 2013167996 A1 | 11/2013 |
| WO | 2015073527 A1 | 5/2015 |
| WO | 2018069907 A1 | 4/2018 |
| WO | 2020058917 A1 | 3/2020 |

OTHER PUBLICATIONS

International Search Report of the International Searching Authority for International Application No. PCT/IB2019/057950 dated Dec. 10, 2019, European Patent Office, Netherlands.
Written Opinion of the International Searching Authority for International Application No. PCT/IB2019/057950 dated Dec. 10, 2019, European Patent Office, Netherlands.
Latif, N., et al., "(Nitroethenyl)salicylic Acid Anilides and Related Substances, a New Group of Mulluscicidal and Mircrobicidal Compounds," Liblings Ann. Chem 1985, p. 1202-1209.
"Anti-Inflammatory Activity of Aspirin—It's All About Salicylic Acid" Retrieved from www.cas.org/news/insights/science-connections/aspirin CAS, Retrieved on Dec. 12, 2017.
Hausen, B., et al., "Inhibition of Thromboxane A2 and Platelet Adhesion with Salicylic Acid Effectively Ameliorates Reperfusion Injury Following Acute Double Lung Transplantation in the Rat," Journal of Heart and Lung Transplantation, Mosby-Year Book, Inc, 18(1): 79-80, Jan. 1, 1999.
International Search Report for International Application No. PCT/IB17/056417 dated Dec. 20, 2017, European Patent Office, Netherlands.
Written Opinion of the International Searching Authority for International Application No. PCT/IB17/056417 dated Dec. 20, 2017, European Patent Office, Netherlands.
J. Colca, "Insulin sensitizers may prevent metabolic inflammation," Biochem Pharm. 72:125-131, (2006).
Min, Jin-Young and Jang, Yong Ju, "Macrolide Therapy in Respiratory Viral Infections," Mediators of Inflammation, pp. 1-9, (2012).
Yuan, M. et al.: "Reversal of Obesity and Diet-Induced Insulin Resistance With Salicylates OrTargeted Disruption of IKKbeta", Science, American Associate for the advancement of Science, US, vol. 293, No. 5535; Aug. 31, 2001.
Certified Copy of Notice of Allowance for Japanese Patent Application No. 2019-541901 dated Jun. 22, 2021 from the Japanese Patent Office .
Chinese First Office Action dated Feb. 23, 2022, issued by the Chinese National Intellectual Property Administration, 9 pages.

* cited by examiner

*Primary Examiner* — Kevin E Weddington
(74) *Attorney, Agent, or Firm* — Cozen O'Connor

(57) ABSTRACT

Methods of treating acute and chronic inflammatory conditions, tissue transplant rejection, and/or organ transplant rejection comprising administering to a subject in need thereof a therapeutically effective amount of a pluripotent anti-inflammatory and metabolic modulators optionally in combination with one or more secondary therapeutic agents and pharmaceutical compositions thereof.

16 Claims, 17 Drawing Sheets

SANA INHIBITS LPS-INDUCED NUCLEAR TRANSLOCATION OF NF-kB/p65 IN THP-1 CELLS AT 10 TIMES LESS CONCENTRATION THAN SA

Fig X. Phase two enzymes Nrf2/Keap1-dependent gene expression. Hep G2 cells were treated with SANA (0.1 mM) or Salicylic Acid (0.2 and 5 mM) for five hours. mRNA was extracted from the cells and was measured HO-1, GCLM and NQO1 gene expression by qPCR.

FIG. 8.
INFLAMMASOME MODULATION BY SANA
Compounds applied at 1st signal
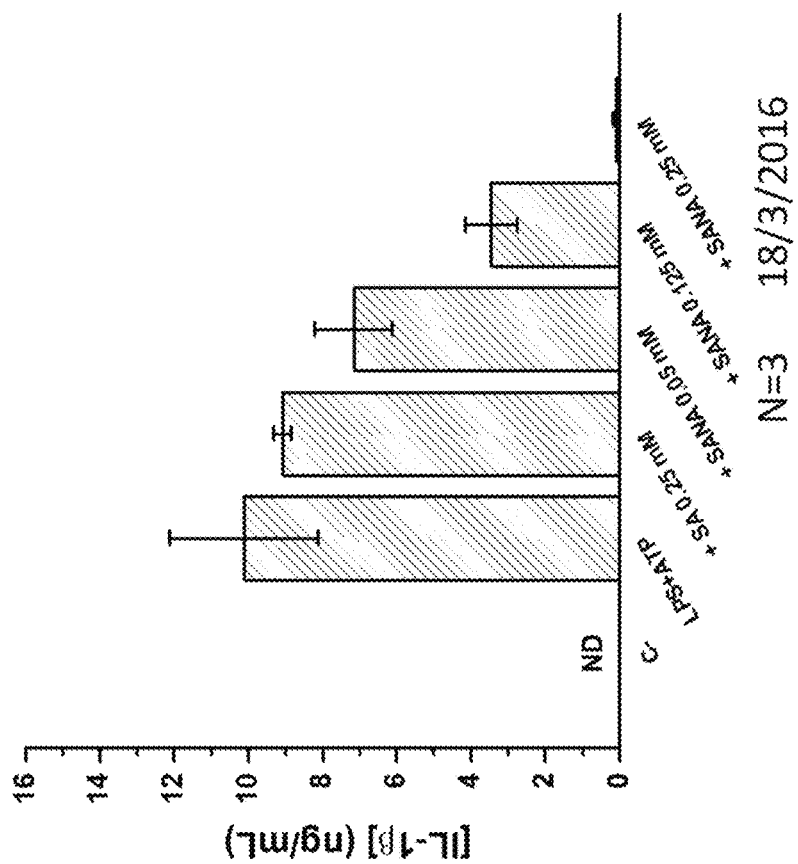
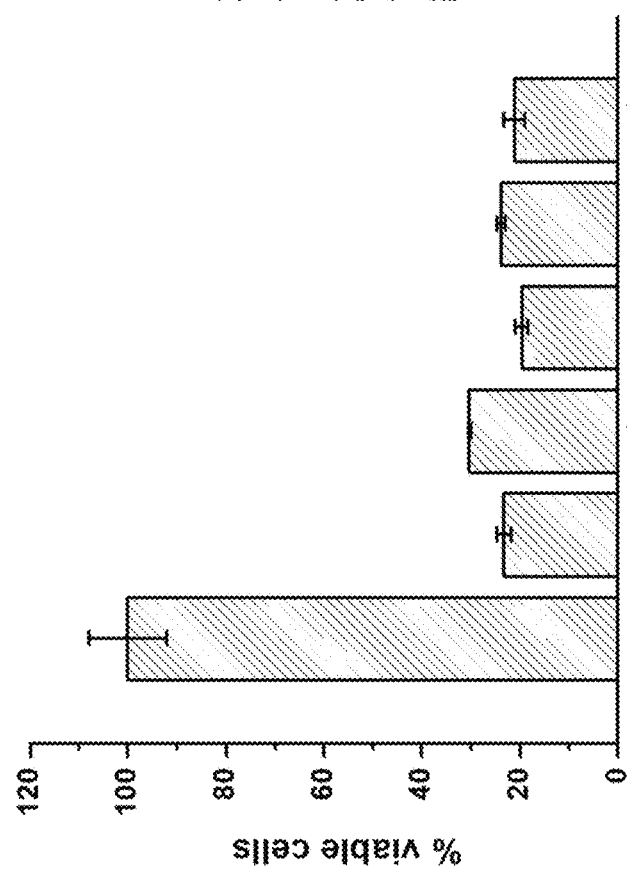

FIG. 9.
INFLAMMASOME MODULATION BY SANA
Compounds applied at 2nd signal
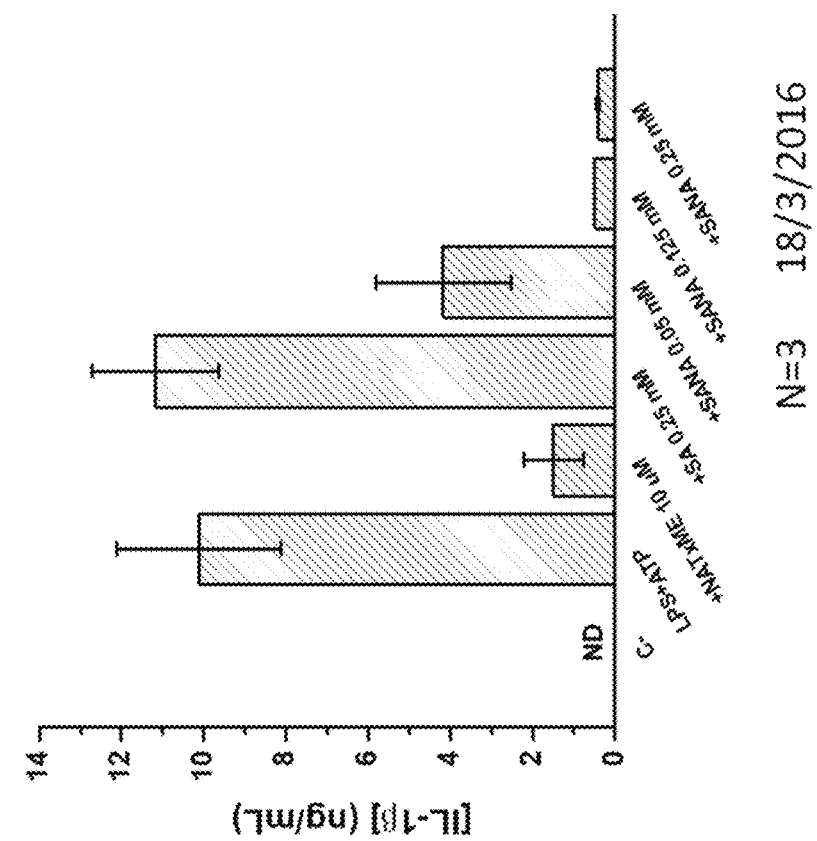
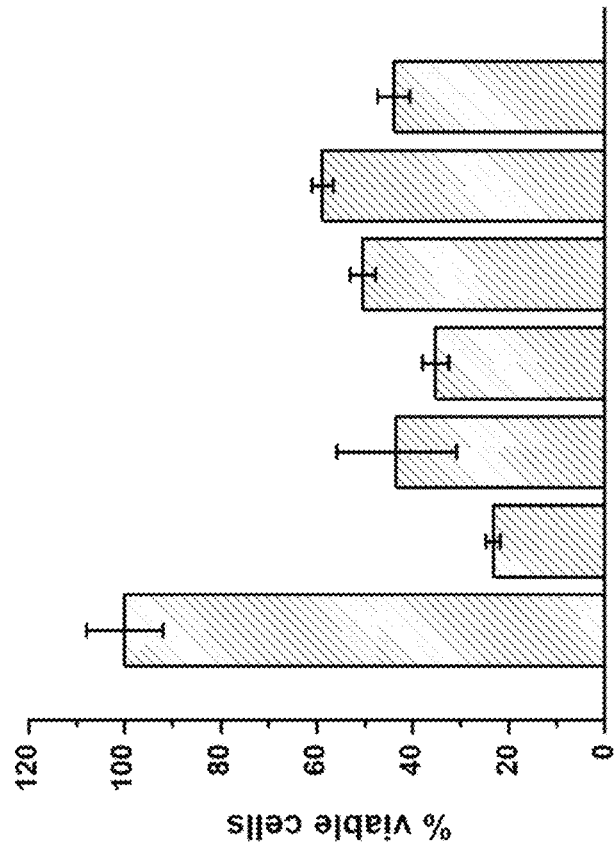

FIG. 10.

ACTIVE AMPK DETECTION IN MICE TREATED WITH SANA

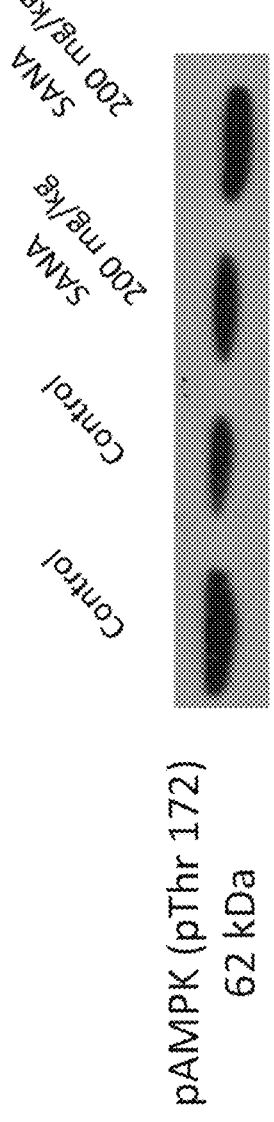
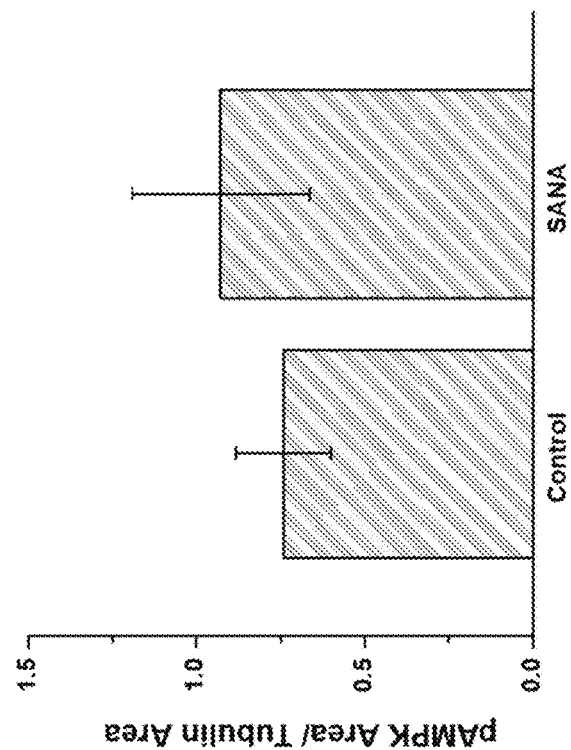

Fig. X. Effect of SANA on AMPK phosphorylation in vivo. C57BL/6 mice were treated with SANA (200 mg/kg, gavage) or PBS ($Na_2HPO_4$ 76 mM; $NaH_2PO_4$ 24 mM; NaCl 17 mM pH 7.4. One hour after administration, livers were extracted and then were homogenized into NETN lysis buffer. pAMPK was then detected by Western blot. Each condition was studied in two mice (n=2).

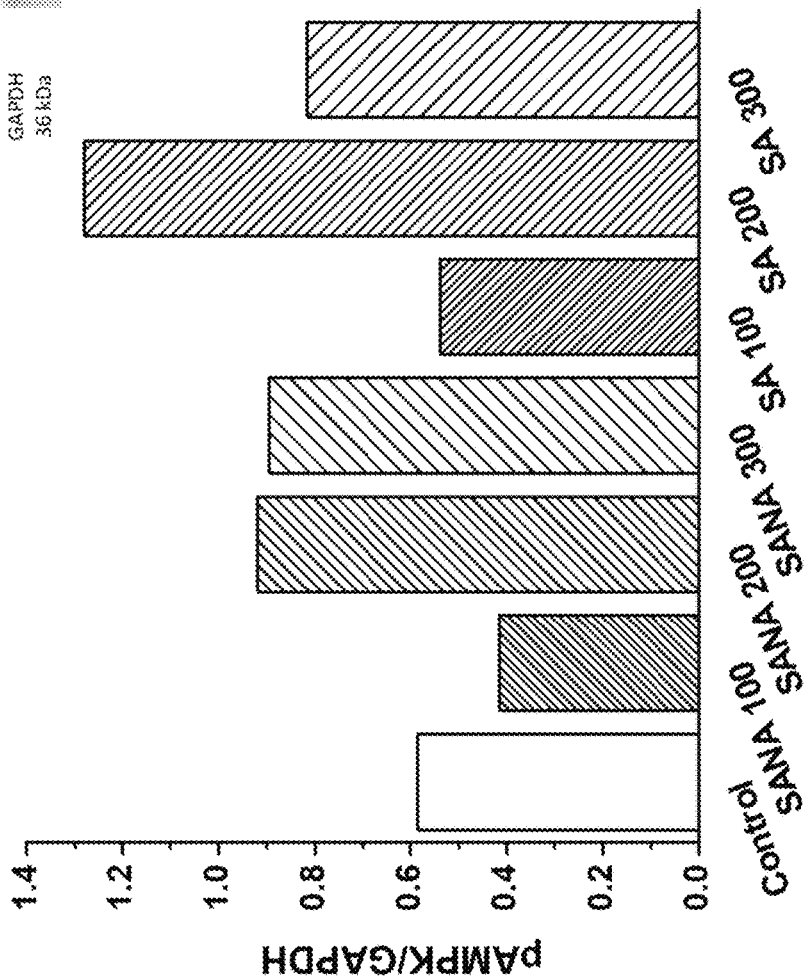
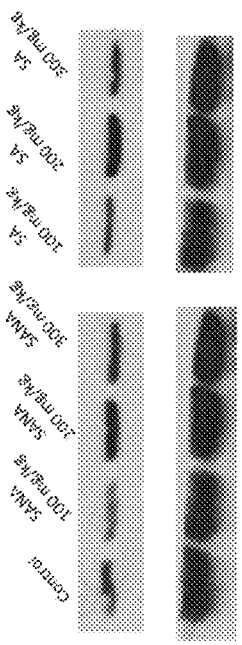
FIG. 11.
Fig. X. Effect of SANA on AMPK phosphorylation in vivo. C57BL/6 mice were treated with SANA (100, 200 and 300 mg/kg, intraperitoneal) or PBS, pH 7.4 ($Na_2HPO_4$ 76 mM; $NaH_2PO_4$ 24 mM; NaCl 17 mM). Two hours after administration, livers were extracted and then were homogenized into NETN lysis buffer. pAMPK was then detected by western blot. Each condition was studied in one mouse (n=1).

Fig. X. Effect of SANA on AMPK phosphorylation in vivo. C57BL/6 mice were treated with SANA (100, 200 and 300 mg/kg, intraperitoneal) or PBS, pH 7.4 ($Na_2HPO_4$ 76 mM; $NaH_2PO_4$ 24 mM; NaCl 17 mM). Two hours after administration, livers were extracted and then were homogenized into NETN lysis buffer. pAMPK was then detected by western blot. Each condition was studied in one mouse (n=1).

Glucose tolerance test. Mice under HFD for up to 7 months (mean weight around 40 gr.) were treated with SANA (100mg/kg gavage) or phosphate buffer (control) every day during four weeks. GTT was performed as usually. Note: GTT before treatment showed no differences between groups

SANA DOES NOT INHIBIT GAPDH ACTIVITY WHILE OTHER NITROALKENE DO

Batthyány, C. et al; J Biol Chem 2006, 281 (29): 20450-63

METHODS OF TREATMENT OF INFLAMMATION RELATED CONDITIONS USING PLURIPOTENT ANTI-INFLAMMATORY AND METABOLIC MODULATORS

CROSS REFERENCE TO RELATED APPLICATIONS

This application is a continuation of patented U.S. application Ser. No. 15/784,685 filed on Oct. 16, 2017, now U.S. Pat. No. 10,537,537, issued on Jan. 21, 2020, which claims the benefit of U.S. Provisional Application No. 62/408,459 filed on Oct. 14, 2016 and U.S. Provisional Application No. 62/570,973 filed on Oct. 11, 2017.

BACKGROUND

Acute and chronic inflammation appears to underlie most, if not all, the chronic diseases of today, including cardiovascular disease, type 2 diabetes, chronic kidney disease, Alzheimer's disease and cancer [1]. However, classical anti-inflammatory drugs—including non-steroidal anti-inflammatory drugs (NSAIDs) and steroidal anti-inflammatory drugs (SAIDs)—are not indicated as part of the regular treatment for these diseases. Common treatments include anti-platelet agents, inhibitors of angiotensin II, insulin sensitizers, HMG-CoA reductase inhibitors and beta blockers. Moreover, classical NSAIDS and SAIDs did not show any benefit, if not adverse effect, in the treatment of cardiovascular, metabolic, neurodegenerative, cancer and chronic kidney diseases [2]. Thus, embodiments of the invention described herein encompass anti-inflammatory treatments of low grade chronic inflammation that underlie most of the chronic non-transmissible diseases of todays.

SUMMARY

One embodiment within the scope of the invention is a method of treating acute and chronic inflammatory conditions comprising administering to a subject in need thereof a therapeutically effective amount of a compound of Formula I:

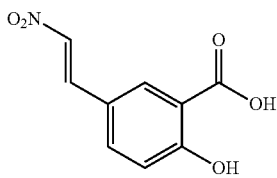

or a pharmaceutically acceptable salt thereof.

In another embodiment the invention is a method of treating inflammation related conditions comprising administering to a subject in need thereof a therapeutically effective amount of a compound of Formula I:

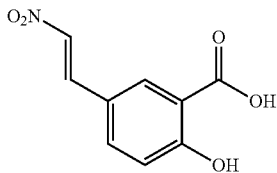

or a pharmaceutically acceptable salt, and a secondary therapeutic agent.

One embodiment within the scope of the invention is a method of treating tissue allograft rejection comprising administering to a subject in need thereof a therapeutically effective amount of a compound of Formula I:

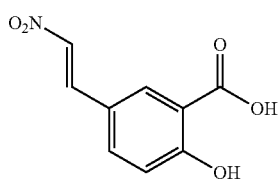

or a pharmaceutically acceptable salt thereof.

In another embodiment within the scope of the invention is a method of treating organ transplant rejection comprising administering to a subject in need thereof a therapeutically effective amount of a compound of Formula I:

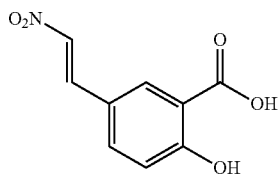

or a pharmaceutically acceptable salt thereof.

In one embodiment, the method of treating organ transplant rejection comprises the treatment of skin allograft rejection comprising administering to a subject in need thereof a therapeutically effective amount of a compound of Formula I:

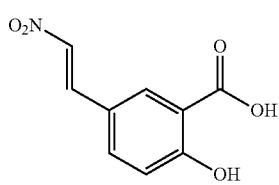

or a pharmaceutically acceptable salt thereof.

DESCRIPTION OF THE DRAWINGS

In FIGS. 8 and 9 show the inhibition of inflammasome in THP-1 cells differentiated into macrophages (PMA 200 nM, 48 hs.) by SANA but not by salicylic acid.

FIG. 10 shows the effect of SANA on AMPK phosphorylation in vivo.

FIG. 11 illustrates the pAMPK phosphorylation levels of SANA compared to salicylic acid in mouse livers at dosage levels from about 100 mg/kg to about 300 mg/kg.

DESCRIPTION

Figure 1:
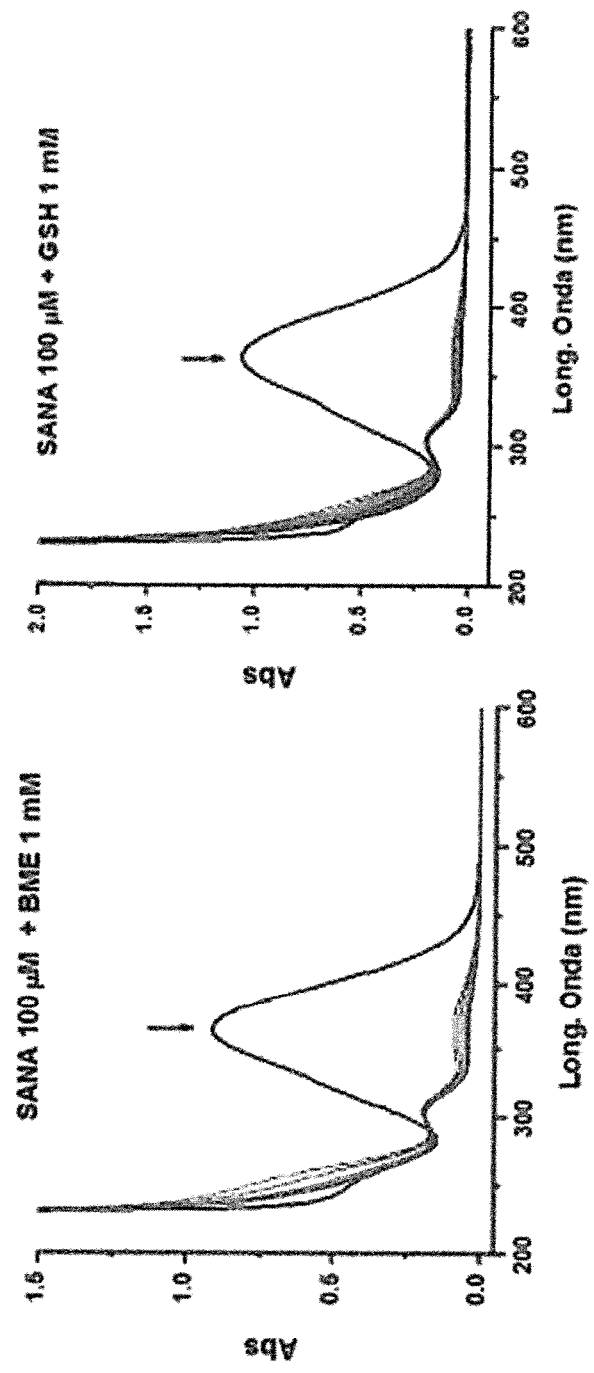
FIG. 1 demonstrates adduct formation of SANA with β-mercaptoethanol (BME) and Gutathione (GSH).

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 5% of the numerical value of the number with which it is being used. Therefore, about 50% means in the range of 45%-55%.

"Administering" when used in conjunction with a therapeutic means to administer a therapeutic directly to a subject, whereby the agent positively impacts the target. "Administering" a composition may be accomplished by, for example, injection, oral administration, topical administration, or by these methods in combination with other known techniques. Such combination techniques include heating, radiation, ultrasound and the use of delivery agents. When a compound is provided in combination with one or more other active agents (e.g. other anti-atherosclerotic agents such as the class of statins), "administration" and its variants are each understood to include concurrent and sequential provision of the compound or salt and other agents.

By "pharmaceutically acceptable" it is meant the carrier, diluent, adjuvant, or excipient must be compatible with the other ingredients of the formulation and not deleterious to the recipient thereof.

"Composition" as used herein is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

As used herein, the term "agent," "active agent," "therapeutic agent," or "therapeutic" means a compound or composition utilized to treat, combat, ameliorate, prevent or improve an unwanted condition or disease of a patient. Furthermore, the term "agent," "active agent," "therapeutic agent," or "therapeutic" encompasses a combination of one or more of the compounds of the present invention.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refer to both therapeutic treatment and prophylactic or preventative measures, wherein the object is to prevent or slow down (lessen) an undesired physiological condition, disorder, or disease, or to obtain beneficial or desired clinical results. For the purposes of this invention, beneficial or desired results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease. Treatment includes prolonging survival as compared to expected survival if not receiving treatment.

The term "subject," as used herein, describes an organism, including mammals, to which treatment with the compositions and compounds according to the subject disclosure can be administered. Mammalian species that can benefit from the disclosed methods include, but are not limited to, apes, chimpanzees, orangutans, humans, monkeys; and other animals such as dogs, cats, horses, cattle, pigs, sheep, goats, chickens, mice, rats, guinea pigs, and hamsters. Typically, the subject is a human.

The term "tissue," as used herein, describes an aggregate of cells typically of a particular kind together with their intercellular substance that form one of the structural materials of a subject. The term "organ," as used herein, describes a group of tissues that perform a specific function. For example, skin is a type of organ embodied herein.

Administration and Compositions

The compounds and pharmaceutically-acceptable salts thereof can be administered by means that produces contact of the active agent with the agent's site of action. They can be administered by conventional means available for use in conjunction with pharmaceuticals in a dosage range of 0.001 to 1000 mg/kg of mammal (e.g. human) body weight per day in a single dose or in divided doses. One dosage range is 0.01 to 500 mg/kg body weight per day orally in a single dose or in divided doses. Administration can be delivered as individual therapeutic agents or in a combination of therapeutic agents. They can be administered alone, but typically are administered with a pharmaceutically acceptable excipient selected on the basis of the chosen route of administration and standard pharmaceutical practice.

Compounds can be administered by one or more ways. For example, the following routes may be utilized: oral, parenteral (including subcutaneous injections, intravenous, intramuscular, intrasternal injection or infusion techniques), inhalation, buccal, sublingual, or rectal, in the form of a unit dosage of a pharmaceutical composition containing an effective amount of the compound and optionally in combination with one or more pharmaceutically-acceptable excipients such as stabilizers, anti-oxidants, lubricants, bulking agents, fillers, carriers, adjuvants, vehicles, diluents and other readily known excipients in standard pharmaceutical practice.

Liquid preparations suitable for oral administration (e.g. suspensions, syrups, elixirs and other similar liquids) can employ media such as water, glycols, oils, alcohols, and the like. Solid preparations suitable for oral administration (e.g. powders, pills, capsules and tablets) can employ solid excipients such as starches, sugars, kaolin, lubricants, binders, disintegrating agents, antioxidants and the like.

Parenteral compositions typically employ sterile water as a carrier and optionally other ingredients, such as solubility aids. Injectable solutions can be prepared, for example, using a carrier comprising a saline solution, a glucose solution or a solution containing a mixture of saline and glucose. Further guidance for methods suitable for use in preparing pharmaceutical compositions is provided in *Remington: The Science and Practice of Pharmacy*, 21$^{st}$ edition (Lippincott Williams & Wilkins, 2006).

Therapeutic compounds can be administered orally in a dosage range of about 0.001 to 1000 mg/kg of mammal (e.g. human) body weight per day in a single dose or in divided doses. One dosage range is about 0.01 to 500 mg/kg body weight per day orally in a single dose or in divided doses. For oral administration, the compositions can be provided in the form of tablets or capsules containing about 1.0 to 500 mg of the active ingredient, particularly about 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In view of the factors affecting the specific dose level and frequency it is contemplated that the dose frequency can range from multiple doses daily to monthly dosages. The preferred dose frequency ranges from twice a day to every two weeks. A more preferred dose frequency ranges from twice a day to weekly. A most preferred dose frequency ranges from twice a day to twice a week.

In the methods of various embodiments, pharmaceutical compositions including the active agent can be administered to a subject in an "effective amount." An effective amount may be any amount that provides a beneficial effect to the patient, and in particular embodiments, the effective amount is an amount that may 1) prevent the subject from experiencing one or more adverse effects associated with a administered agents, such as those used to diagnose, identify, and treat medical conditions, 2) reduce side effects experienced by the subject as a result of a medical therapy or reduce the side effects known to result from such therapies, and/or 3) eliminate side effects resulting from a medical treatment experienced by the subject prior to administration of the active agent or eliminate the side effects known to result from such treatment. An effective amount may further be any amount that provides a beneficial effect to the patient, and in particular embodiments, the effective amount is an amount that may 1) prevent or reduce rejection of tissue allografts and/or 2) prevent or reduce rejection of a transplanted organ.

Pharmaceutical formulations containing the compounds of the invention and a suitable carrier can be in various forms including, but not limited to, solids, solutions, powders, fluid emulsions, fluid suspensions, semi-solids, and dry powders including an effective amount of an the active agent of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's, The Pharmaceutical Basis of Therapeutics*, 6th Edition, MacMillan Publishing Co., New York (1980) both of which are hereby incorporated by reference in their entireties can be consulted.

Other embodiments of the invention include the active agent prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

In another exemplary embodiment, an oily preparation of an active agent prepared as described above may be lyophilized to form a solid that may be mixed with one or more pharmaceutically acceptable excipient, carrier or diluent to form a tablet, and in yet another embodiment, the active agent may be crystallized to from a solid which may be combined with a pharmaceutically acceptable excipient, carrier or diluent to form a tablet.

The means and methods for tableting are known in the art and one of ordinary skill in the art can refer to various references for guidance. For example, *Pharmaceutical Manufacturing Handbook: Production and Processes*, Shayne Cox Gad, John Wiley & Sons, Inc., Hoboken, N.J. (2008), which is hereby incorporated by reference in its entirety can be consulted.

Further embodiments which may be useful for oral administration of the active agent include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt. Other suitable diluents include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids may have between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil," refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, microgolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko).

Polyethylene glycol: As used herein, the term "polyethylene glycol" or "PEG" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400.

Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to a monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may be used in the synthesis as well. Suitable stearoyl macrogol glycerides include, but are not limited to, Gelucire® 50/13 (available from Gattefosse).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include the active agent administered in combination with other active such as, for example, adjuvants, protease inhibitors, or other compatible drugs or compounds where such combination is seen to be desirable or advantageous in achieving the desired effects of the methods described herein.

Other embodiments of the present invention include a pharmaceutical composition comprising an effective amount of the active agent and one or more pharmaceutically acceptable excipient. Other embodiments include a pharmaceutical composition comprising an effective amount of pharmaceutically-acceptable salts of the active agent. Other embodiments include a pharmaceutical composition comprising an effective amount of pharmaceutically-acceptable salts of active agent and a pharmaceutically-acceptable excipient.

In yet other embodiments, the active agent may be combined with one or more secondary therapeutic agents. Secondary therapeutic agents my include but are not limited to: an anti-platelet agent, an inhibitor of angiotensin II, an ACE inhibitor, a $Ca^{++}$ channel blocker, an insulin sensitizer, a HMG-CoA reductase inhibitor, a beta blocker, a non-steroidal anti-inflammatory drug, a steroidal anti-inflammatory drug, peroxisome proliferator-activated receptors (PPAR) modulators, and combinations thereof.

Pluripotent anti-inflammatory and metabolic modulators and pharmaceutical compositions thereof as described herein may be administered to subjects to treat a number of both acute and chronic inflammatory and metabolic conditions. In some embodiments, the pluripotent anti-inflammatory and metabolic modulators and pharmaceutical compositions thereof as described herein may be used to treat acute conditions including general inflammation, autoimmune disease, auto-inflammatory disease, arterial stenosis, organ transplant rejection and burns, and chronic conditions such as, chronic lung injury and respiratory distress, diabetes, hypertension, obesity, arthritis, neurodegenerative disorders and various skin disorders.

However, in other embodiments, the pluripotent anti-inflammatory and metabolic modulators and pharmaceutical compositions thereof as described herein may be used to treat any condition having symptoms including chronic or acute inflammation, such as, for example, arthritis, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, lung inflammation, fibrosis of the lung, asthma, acquired respiratory distress syndrome, tobacco induced lung disease, granuloma formation, fibrosis of the liver, graft vs. host disease, postsurgical inflammation, coronary and peripheral vessel restenosis following angioplasty, stent placement or bypass graft, coronary artery bypass graft (CABG), acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, alopecia and the like.

The compound of Formula I and pharmaceutical compositions thereof as described herein may be administered to subjects to treat tissue allograft rejection. In other embodiments, the compound of Formula I and pharmaceutical compositions thereof as described herein may be administered to subjects to prevent or reduce rejection of a transplanted organ. In some embodiments, the compound of Formula I and pharmaceutical compositions thereof as described herein may be used to prolong the survival of a grafted tissue. In some embodiments, the compound of Formula I and pharmaceutical compositions thereof as described herein may be used to prolong the survival of a transplanted organ.

EXAMPLES

The following examples contain detailed methods of preparing compounds of Formula I. These detailed descriptions serve to exemplify the above general synthetic schemes which form part of the invention. These detailed descriptions are presented for illustrative purposes only and are not intended as a restriction on the scope of the invention. All parts are by weight and temperatures are in Degrees Celsius unless otherwise indicated. All compounds showed NMR spectra consistent with their assigned structures.

Example 1: 2-Hydroxy-5-(2-Nitroethenyl)Benzoic Acid (SANA)

To a solution of 5-formylsalicylic (1 g, 6.02 mmol) in ethanol (16.5 mL), nitromethane (5.5 mL, 0.10 mmol) and ammonium acetate (1.39 g, 18.06 mmol) were added. The reaction mixture is heated at 60° C. for h, allowed to cool to room temperature and put in refrigerator for 15 minutes. Formed orange precipitate was filtered off and dissolved in water (ca. 250 mL). Solution was acidified with concentrated HCl (ca. 10 drops) until total precipitation. Formed yellow solid was filtered off and dried in vacuo. Yield: 1.18 g (93%).

1H NMR (acetone-$d_6$): δ=8.35 (d, J=2.3 Hz, 1H), 8.14 (d, J=13.7, 1H), 8.06 (dd, J=8.7 2.3 Hz, 1H), 7.99 (d, J=13.7 Hz, 1H), 7.11 (d, J=8.7 Hz, 1H). 13C NMR (acetone-$d_6$): δ=171.09, 164.66, 137.94, 136.51, 135.94, 133.21, 121.95, 118.51, 113.08

Biologic Activity

The following methods described are used in order to demonstrate biological activity and therapeutic use, and should not to be construed in any way as limiting the scope of the invention.

In Vitro Activity

As shown in FIG. 1, SANA (100 mM) in phosphate buffer 100 mM, pH 7.4 was incubated with β-mercaptoethanol (BME) (1 mM) or Glutathione (GSH) (1 mM) and the reaction was followed spectrophotometrically (1 scan every 1 min for up to 15 min). UV-visible spectra was acquired by a Varian Cary 50 Bio. Scans were taken every min up to 15 min.

The reaction between SANA and BME or GSH showed increased absorption at the 360 nm wavelength. The increase at 360 nm demonstrates adduct formation between SANA and BME or GSH.

Figure 2:
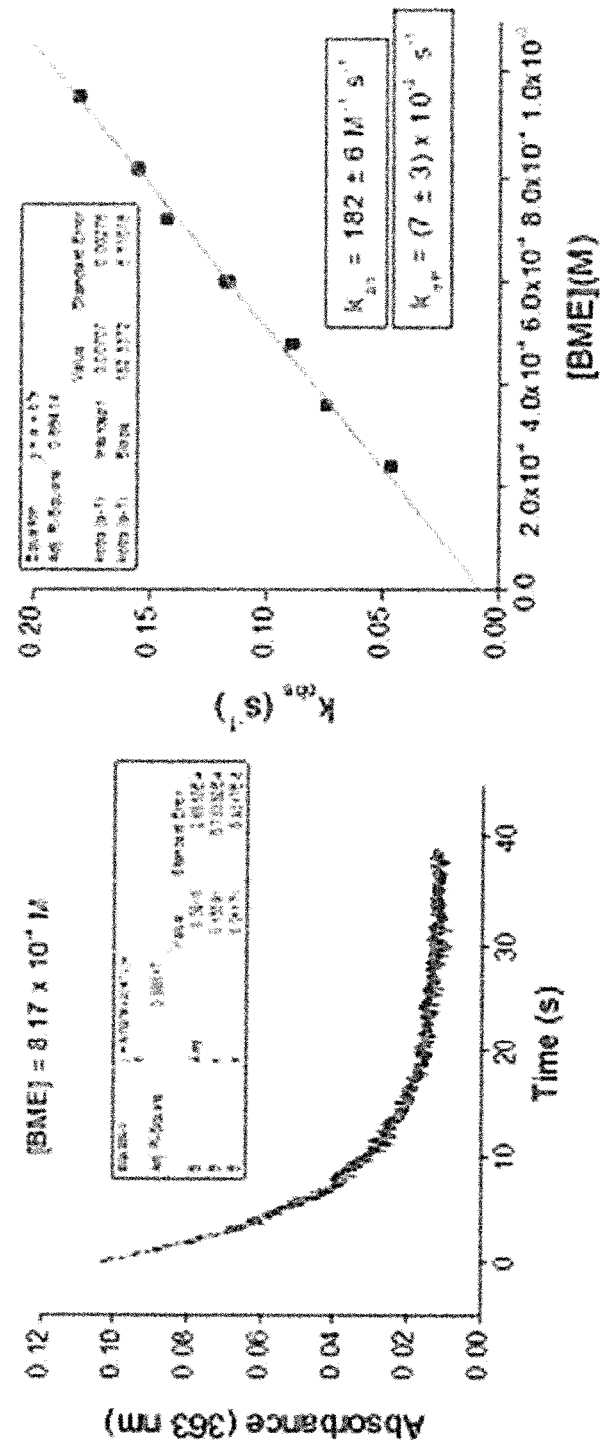
FIG. 2 shows that the reaction between SANA and BME has a second order rate constant.

In FIG. 2, it is shown that the reaction between SANA and BME was determined to be a second order rate constant. Stopped-flow kinetic measurements were performed using an Rx 2000 stopped flow analyzer (Applied Photophysics). Mixtures of 150 μL NATx0 (25 μM) and solutions of BME at 0.54 mM, 1.09 mM, 1.64 mM, 2.18 mM, and 2.73 mM concentrations.

The reaction was monitored by following the absorbance at 260 nm and plots were fitted to a simple exponential decay function using Originlab software (version 8.0). The observed pseudo first order constant at each concentration of BME was extracted from the equation and plotted against the concentration of BME. The second rate constant of the reaction is derived from the slope of the curve and was 182±6 $M^{-1}s^{-1}$. All experiments were carried out at 25° C. by triplicate.

Figure 3:
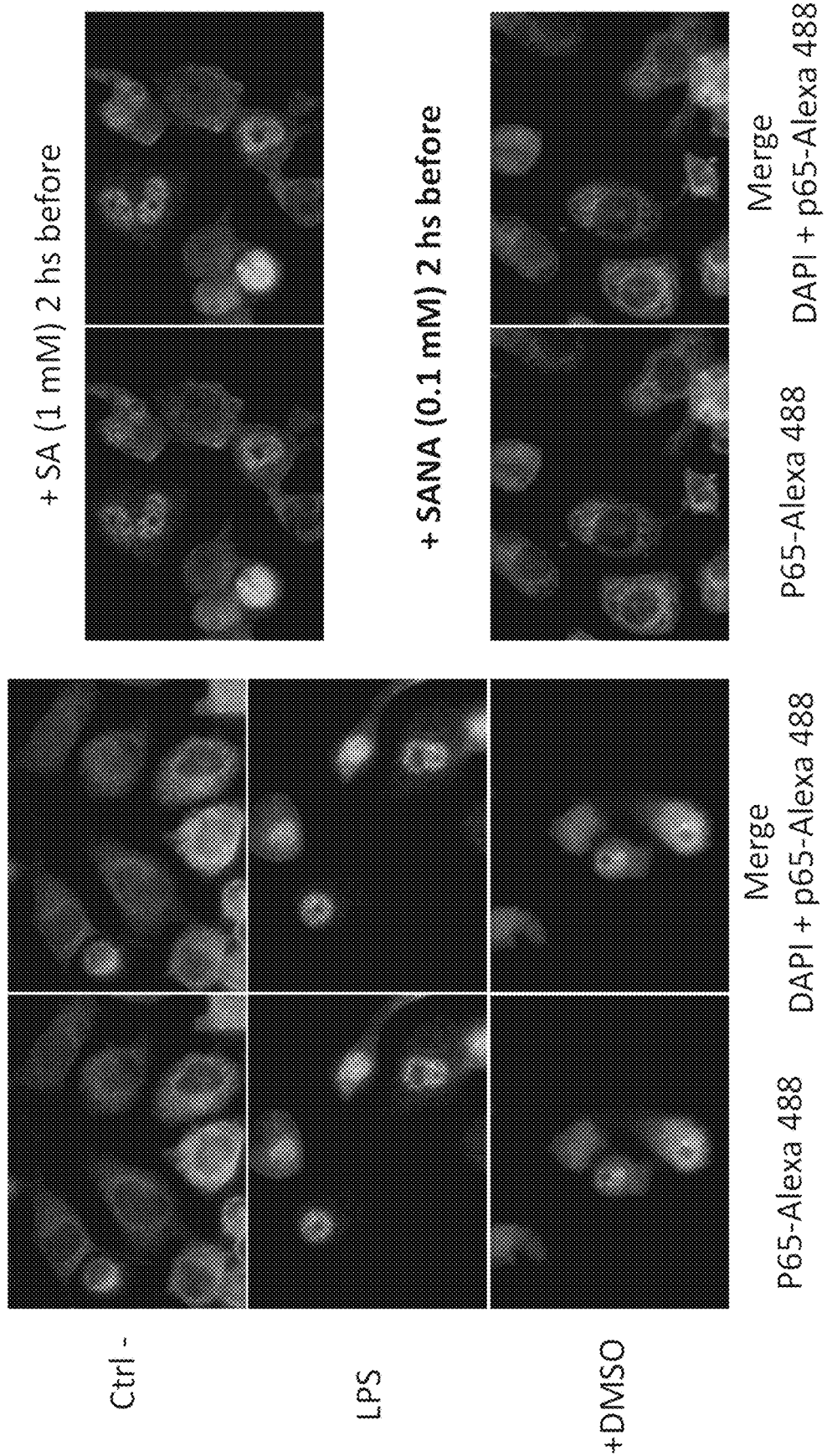
FIG. 3 illustrates the effect of SANA on LPS-induced NF-κB/p65 subcellular localization in THP-1 macrophages.

Nuclear factor kappa B (NF-κB) represents a family of pro-inflammatory transcription factors, present in all eukaryotic cells, which regulate inducible expression of wide ranging genes involved in immune responses and cell-cycle regulation. Activation of NF-κB is accompanied by nuclear translocation of NF-κB. Accordingly, FIG. 3 illustrates the lack of nuclear translocation of NF-κB in the presence of SANA to further demonstrate its anti-inflammatory effects. Specifically, FIG. 3 illustrates immunofluorescence and epifluorescence microscopy analysis showing the effect of SANA on LPS-induced NF-κB/p65 subcellular localization in THP-1 macrophages. Unexpectedly, cells treated with SANA at a concentration of 0.1 mM, 2 hs before activation with LPS (1 ug/mL) showed the same effect as cells treated with salicylic acid at 1 mM. This data indicates that SANA was significantly more potent than salicylic acid.

Figure 4:
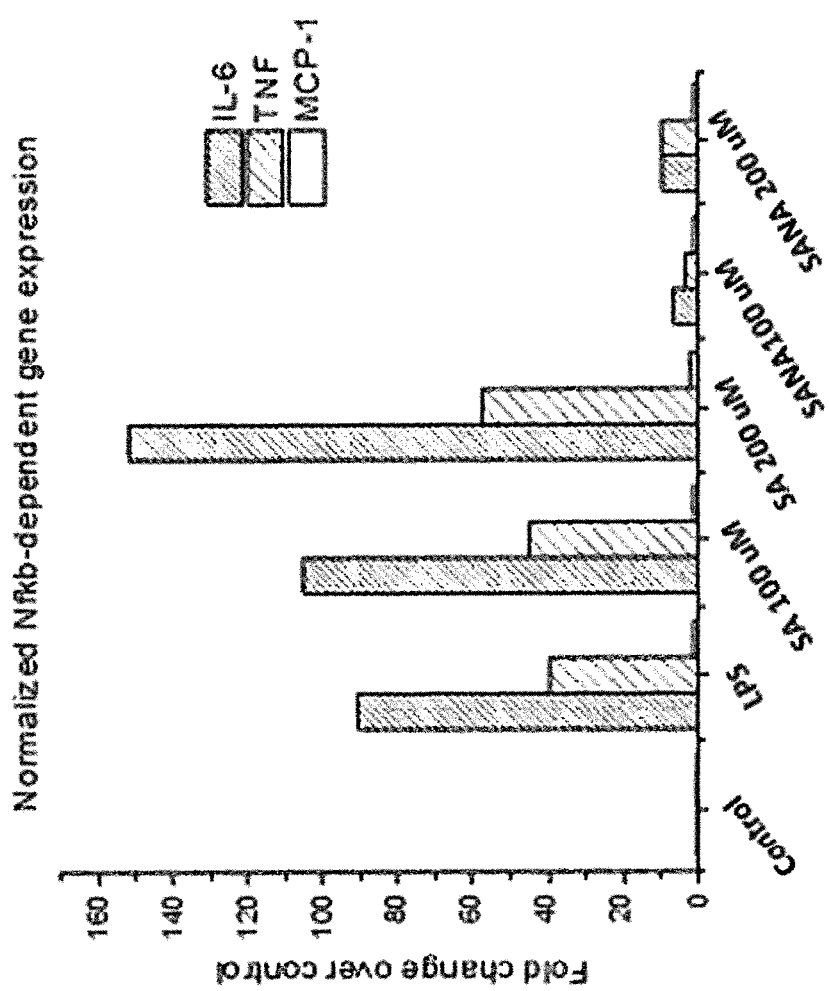
FIG. 4 shows the inhibition of NF-kB-dependent gene expression in human macrophages by SANA.

FIG. 4 shows the inhibition of NF-kB-dependent gene expression in human macrophages by SANA. THP-1 cells were differentiated into macrophages. Cells were then treated with SANA (100 and 200 uM) or Salicylic acid (SA: 100 and 200 uM) for 2 hours. Cells were then stimulated with LPS (1 mg/mL, 3 hours). mRNA was extracted and IL-6, TNF-a and MCP-1 fold change gene expression over control were quantified by qPCR. Interestingly, FIG. 4 shows that when uses at the same concentration, SA was not able to inhibit NF-kB dependent gene expression in these cells.

Figure 5:
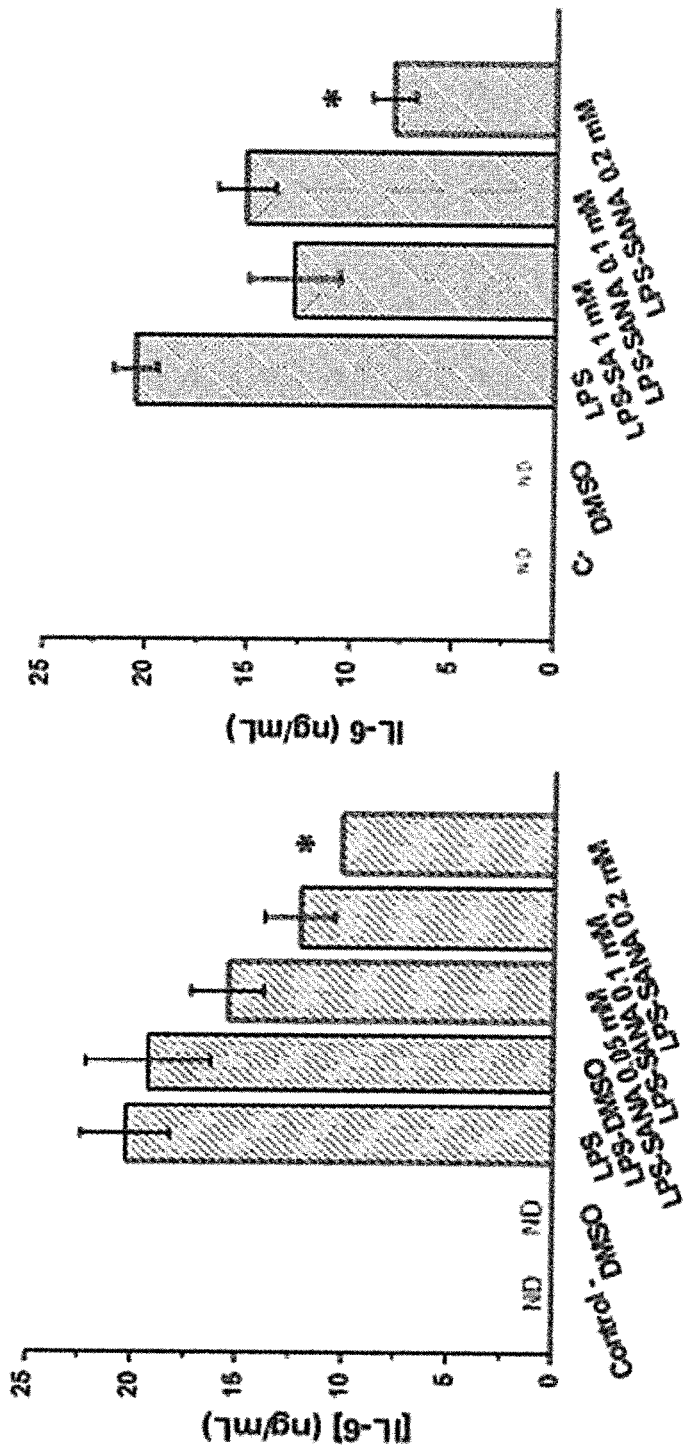
FIG. 5 shows that SANA is a more potent inhibitor of NF-kB dependent gene expression in these cells than salicylic acid.

In FIG. 5 murine RAW 264.7 macrophages were treated with/without SANA (0, 50; 100 and 200 uM, 2 hours) or SA (1 mM) to see the potential inhibition of NF-kB dependent gene expression in murine macrophages. Cells were then stimulated with LPS (50 ng/mL, 16 hours). Supernatants were collected and IL-6 was measured by ELISA. We applied one-way ANOVA statistic test with Bonferroni post-host. (*): p<0.05 compared to LPS-DMSO. FIG. 5. shows that SANA is a more potent inhibitor of NF-kB dependent gene expression in these cells than SA.

Figure 6:
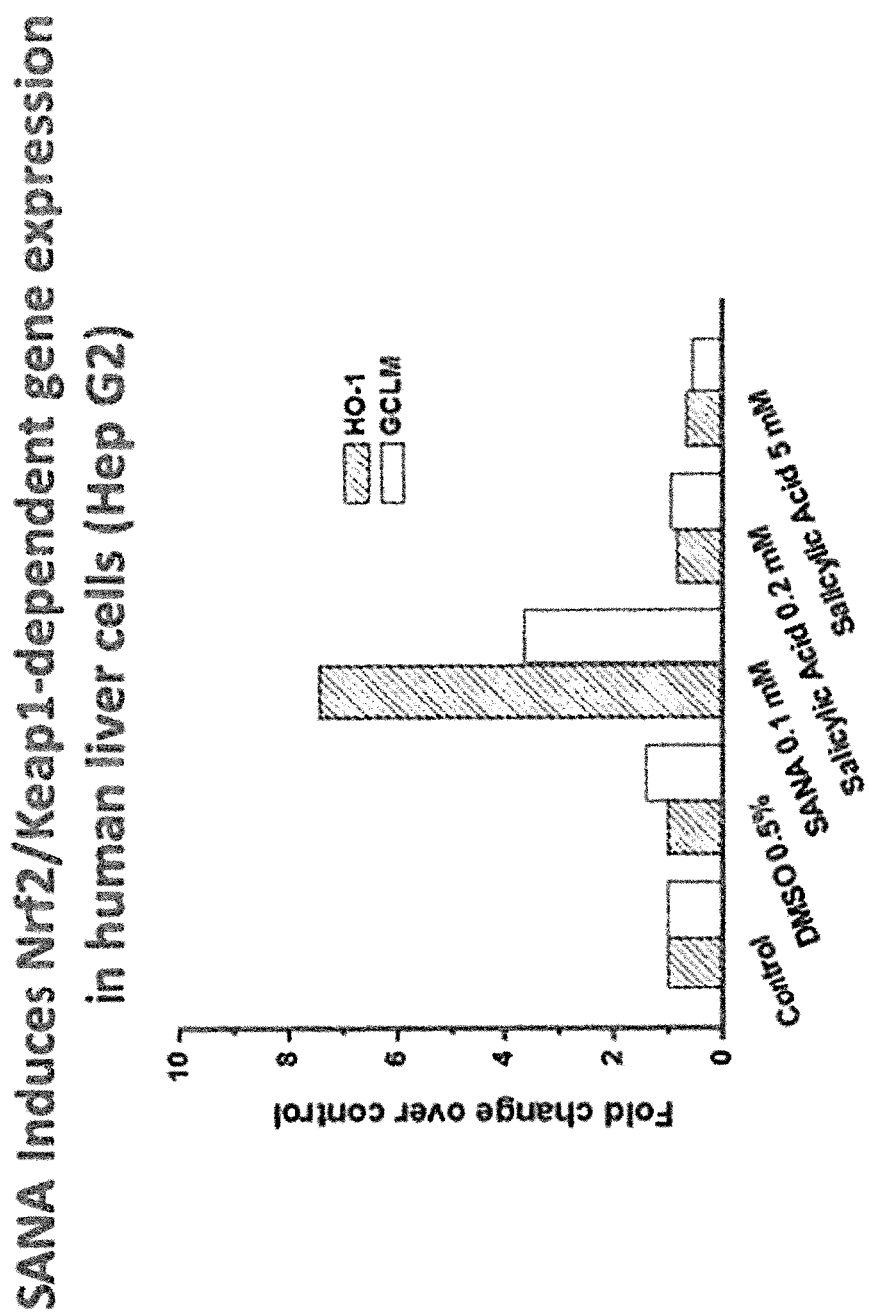
FIGS. 6 and 7 show induction of phase two enzymes Nrf2/Keap 1-dependent gene expression by SANA but not by salicylic acid.
Figure 7:
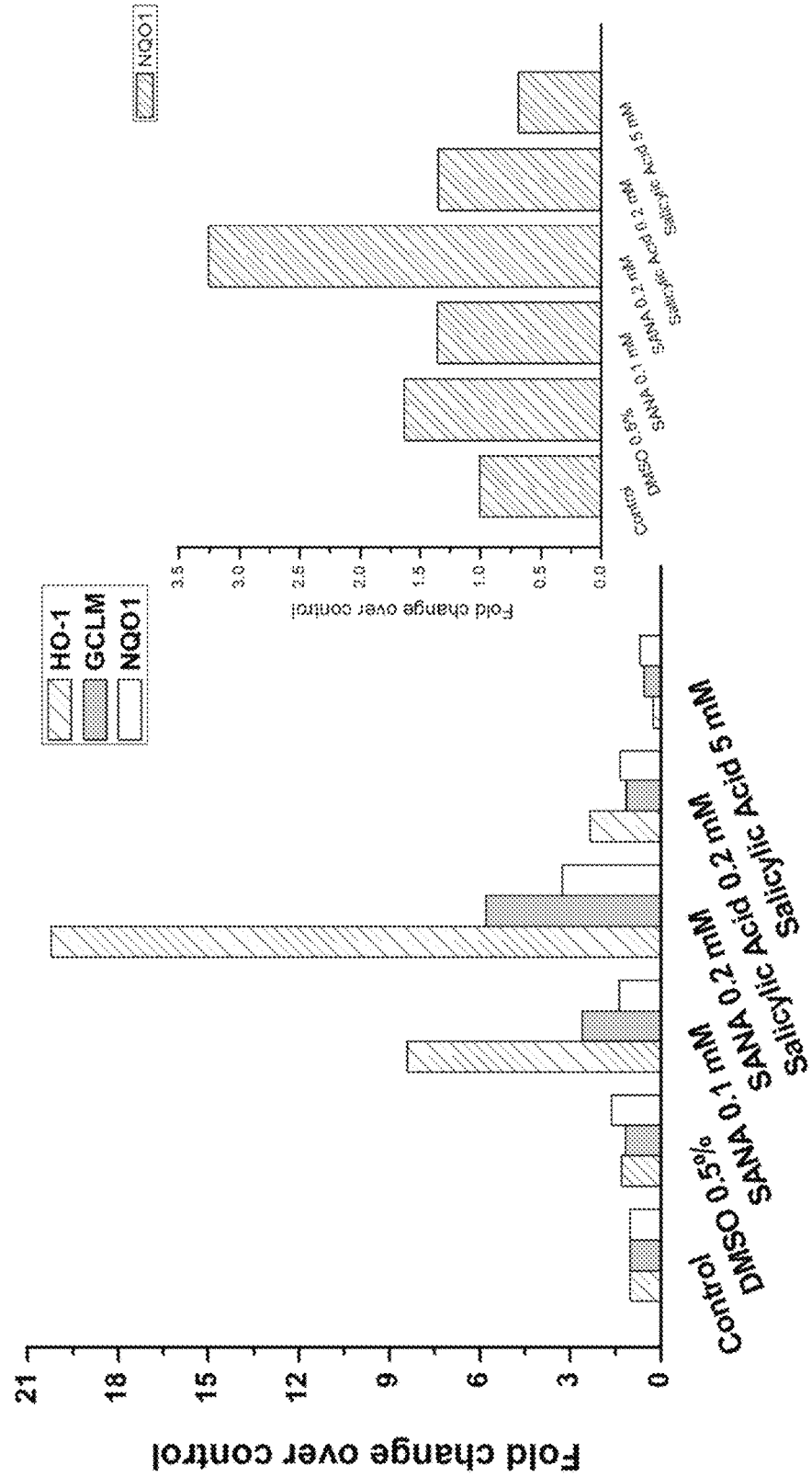

FIGS. 6 and 7 show induction of phase two enzymes Nrf2/Keap 1-dependent gene expression by SANA but not by SA. Hep G2 cells were treated with SANA (0.1 mM) or Salicylic Acid (0.2 and 5 mM) for five hours. mRNA was extracted from the cells and was measured HO-1, GCLM and NQO1 gene expression by qPCR.

In FIGS. 8 and 9 show the inhibition of inflammasome in THP-1 cells differentiated into macrophages (PMA 200 nM, 48 hs.) by SANA but not by SA when applied together with the first (FIG. 8) or the second (FIG. 9) signal. In FIG. 8 cells were treated with Salicylic acid (0.25 mM) or SANA (0.05; 0.125 and 0.25) together with LPS stimulation. The cells were stimulated with LPS (250 ng/mL, 3 hs.) and then with ATP (5 mM, 45 minutes). Supernatant was collected and IL-1b measured by ELISA. Cell viability was assessed by MTT assay. The values are showed as mean±SD.

In FIG. 9 THP-1 cells were differentiated into macrophages with PMA (200 nM, 48 hs.). Cells were stimulated with LPS (250 ng/mL, 3 hs.) and then with ATP (5 mM, 45 minutes). Together with ATP treatment, cells were then treated with NATxME (10 uM), Salicylic acid (0.25 mM) or SANA (0.05; 0.125 and 0.25 mM). Supernatant was collected and IL-1b secretion was measured by ELISA. Cell viability was assessed by the MTT assay. The values are showed as mean±SD. FIGS. 8 and 9 show that SAN is a potent inhibitor of the inflammasome when applied with the first or second signal, whereas SA cannot inhibit this potent pro-inflammatory cellular pathway.

In Vivo Activity

FIG. 10 shows the effect of SANA on AMPK phosphorylation in vivo. C57BL/6 mice were treated with SANA (200 mg/kg, gavage) or PBS ($Na_2HPO_4$ 76 mM; $NaH_2PO_4$ 24 mM; NaCl 17 mM pH 7.4. One hour after administration, livers were extracted and then were homogenized into NETN lysis buffer. pAMPK was then detected by Western blot. Each condition was studied in two mice (n=2).

In FIG. 11 C57BL/6 mice were treated with SANA or SA (100, 200 and 300 mg/kg, intraperitoneal) or PBS, pH 7.4 ($Na_2HPO_4$ 76 mM; $NaH_2PO_4$ 24 mM; NaCl 17 mM). Two hours after administration, livers were extracted and then were homogenized into NETN lysis buffer. pAMPK was then detected by western blot. Each condition was studied in one mouse (n=1).

Figure 12:
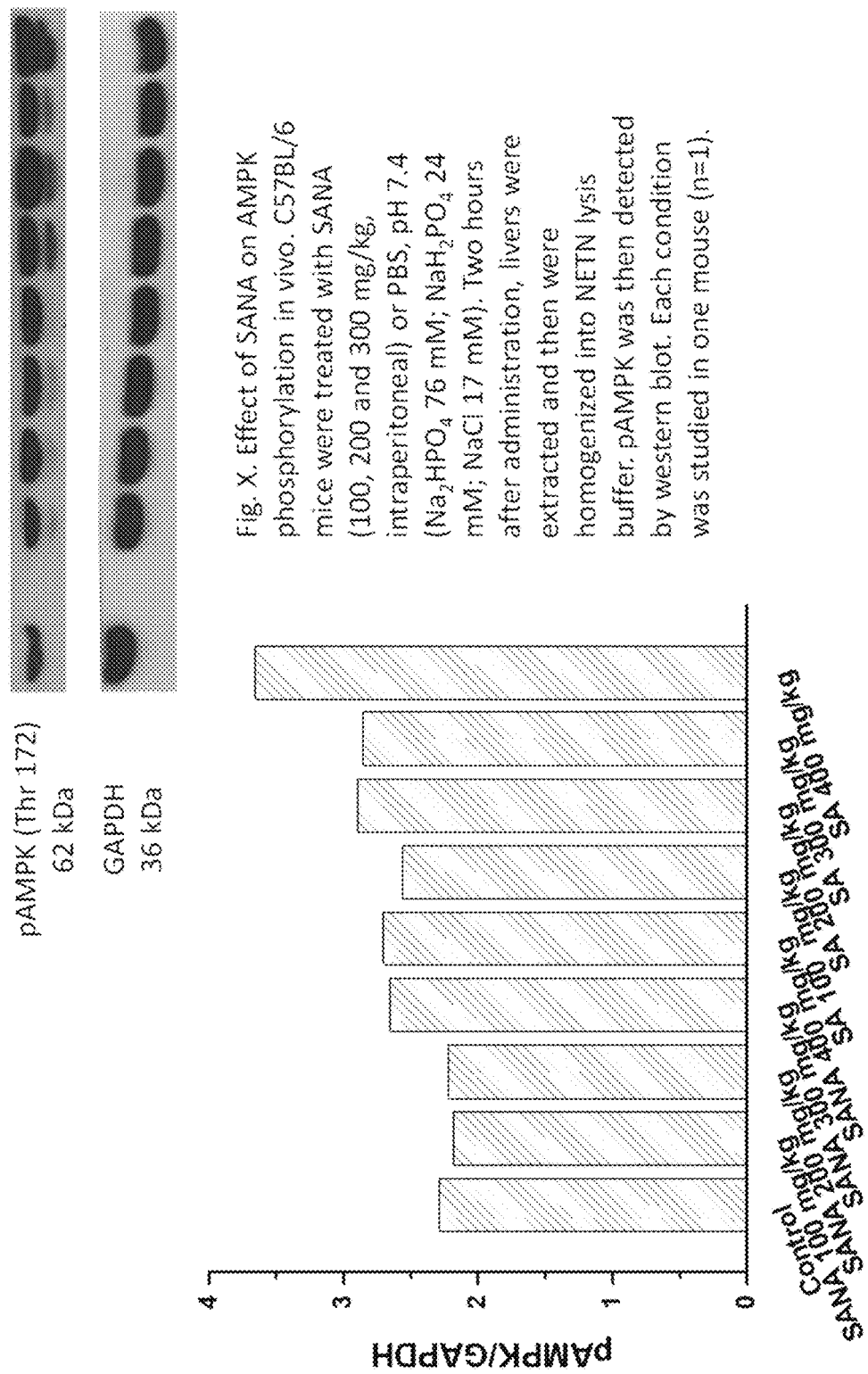
In FIG. 12 illustrates the pAMPK phosphorylation levels of SANA compared to salicylic acid in mouse livers at dosage levels from about 100 mg/kg to about 400 mg/kg.

In FIG. 12 C57BL/6 mice were treated with SANA up to 400 mg/kg intraperitoneally or PBS, pH 7.4 ($Na_2HPO_4$ 76 mM; $NaH_2PO_4$ 24 mM; NaCl 17 mM). Two hours after administration, livers were extracted and then were homogenized into NETN lysis buffer. pAMPK was then detected by western blot. Each condition was studied in one mouse (n=1).

Figure 13:
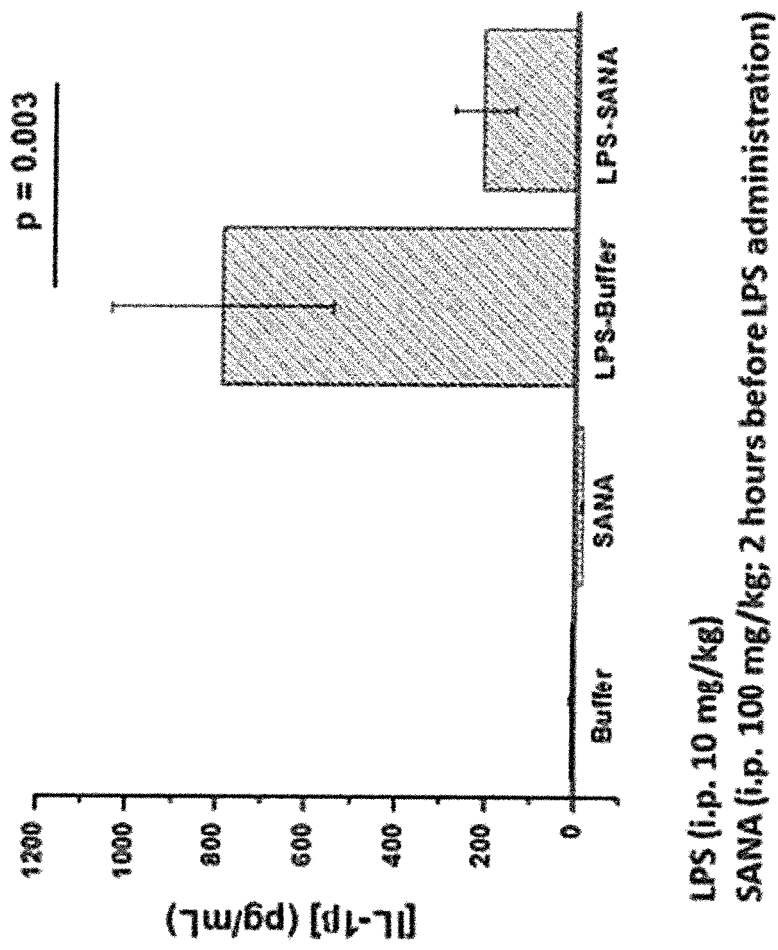
FIG. 13 shows that SANA decreases LPS-induced Il-1b secretion into the peritoneum in vivo.

FIG. 13 shows that SANA decreases LPS-induced Il-1b secretion into the peritoneum in vivo.

Figure 14:
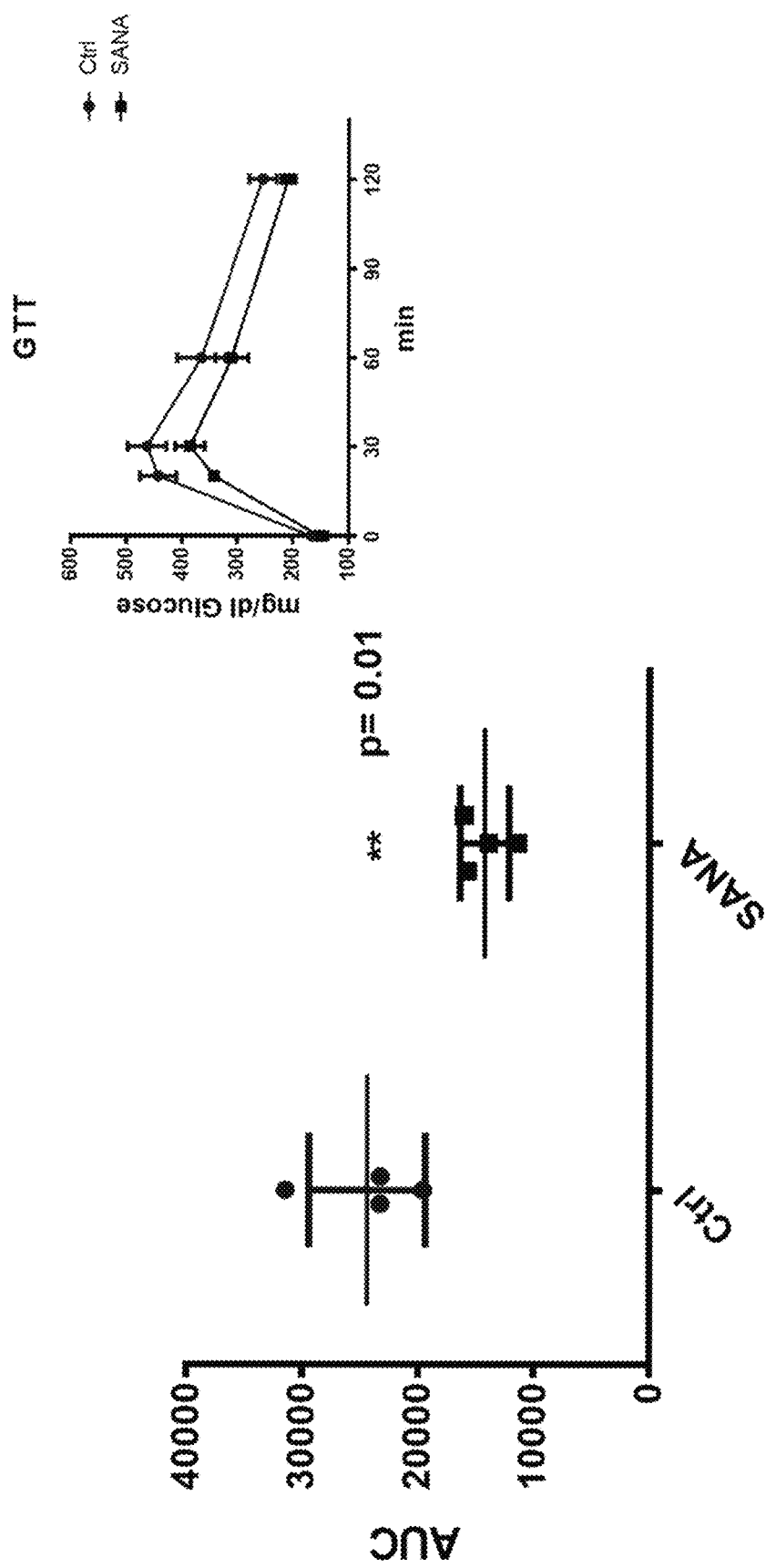
FIG. 14 shows that SANA reverses insulin resistance in HFD-induced obese mice.

FIG. 14 shows that SANA reverses insulin resistance in HFD-induced obese mice. Mice under HFD for up to 7 months (mean weight around 40 gr.) were treated with SANA (100 mg/kg; gavage) or phosphate buffer (control) every day during four weeks. The glucose tolerance test were run as per well-known standard procedures.

Figure 15:
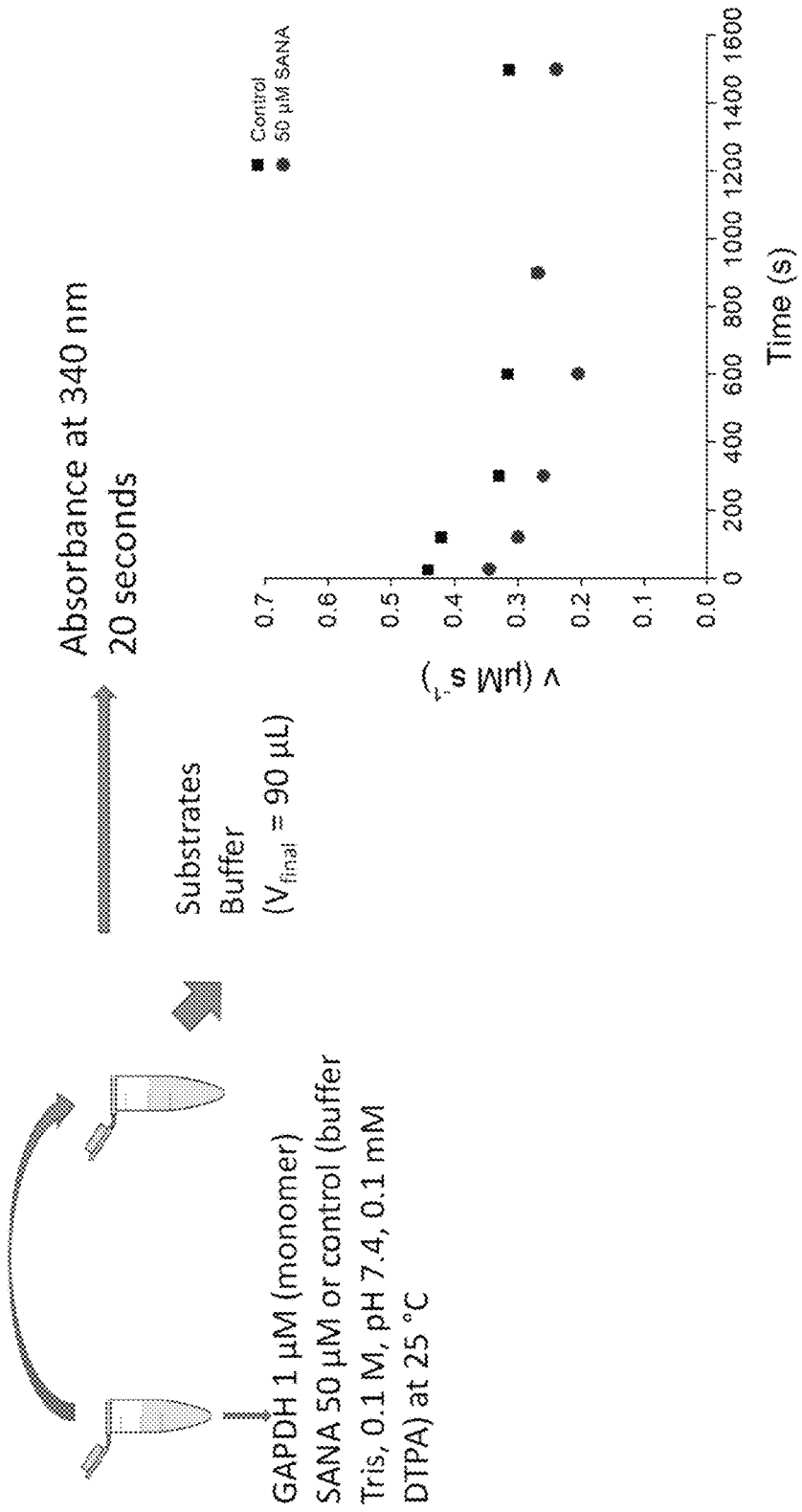
FIG. 15 shows that SANA unexpectedly does not inhibit GAPDH activity while that is commonly observed with nitroalkenes.

FIG. 15 shows that SANA unexpectedly does not inhibit GAPDH activity while that is commonly observed with nitroalkenes.

Figure 16:
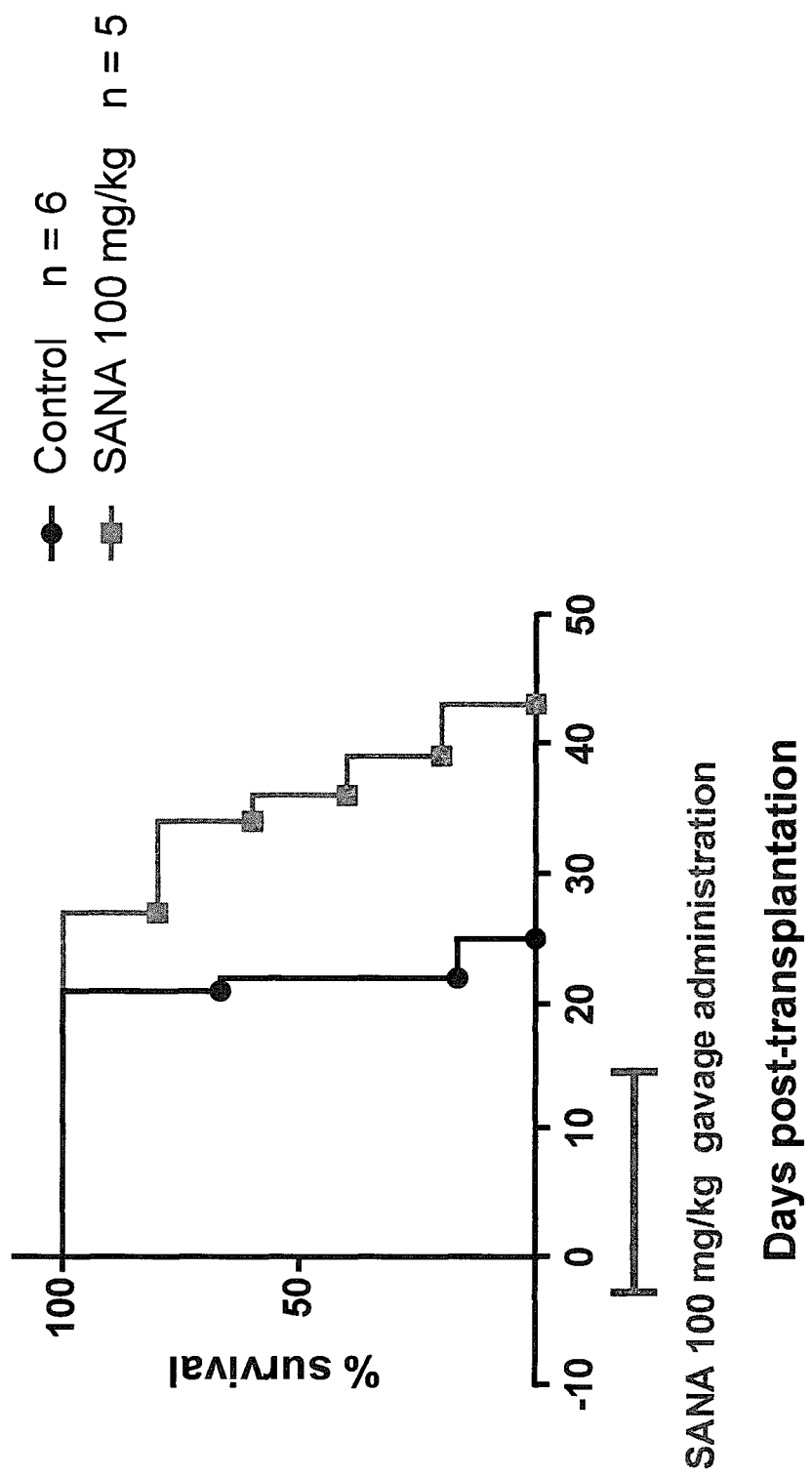
FIG. 16 demonstrates that SANA treated skin allograft rejection better than the control group.

As shown in FIG. 16, administering SANA to subjects demonstrated prolonged survival of grafted skin as compared to a control group. C57BL/6 female mice were grafted with skin from the tails of C57BL/6 male mice. The skin graft is a small square (1 $cm^2$) and it was implanted onto the left subscapular region of the female mice. From one day before the transplantation until 15 days after it, the mice were treated daily with SANA (100 mg/kg, by oral gavage; SANA group) or vehicle (Control group). The vehicle used was a solution of Carboxy-Methyl-cellulose 0.5% m/v and Tween 80 0.5% v/v. At the end of the 15th day of administration, allografts were checked every 48/72 hours to assess the condition of the grafted skin. Rejection was diagnosed clinically when the allograft lost more than 50% of its size and/or more than 10% of allograft was necrotic.

Figure 17:
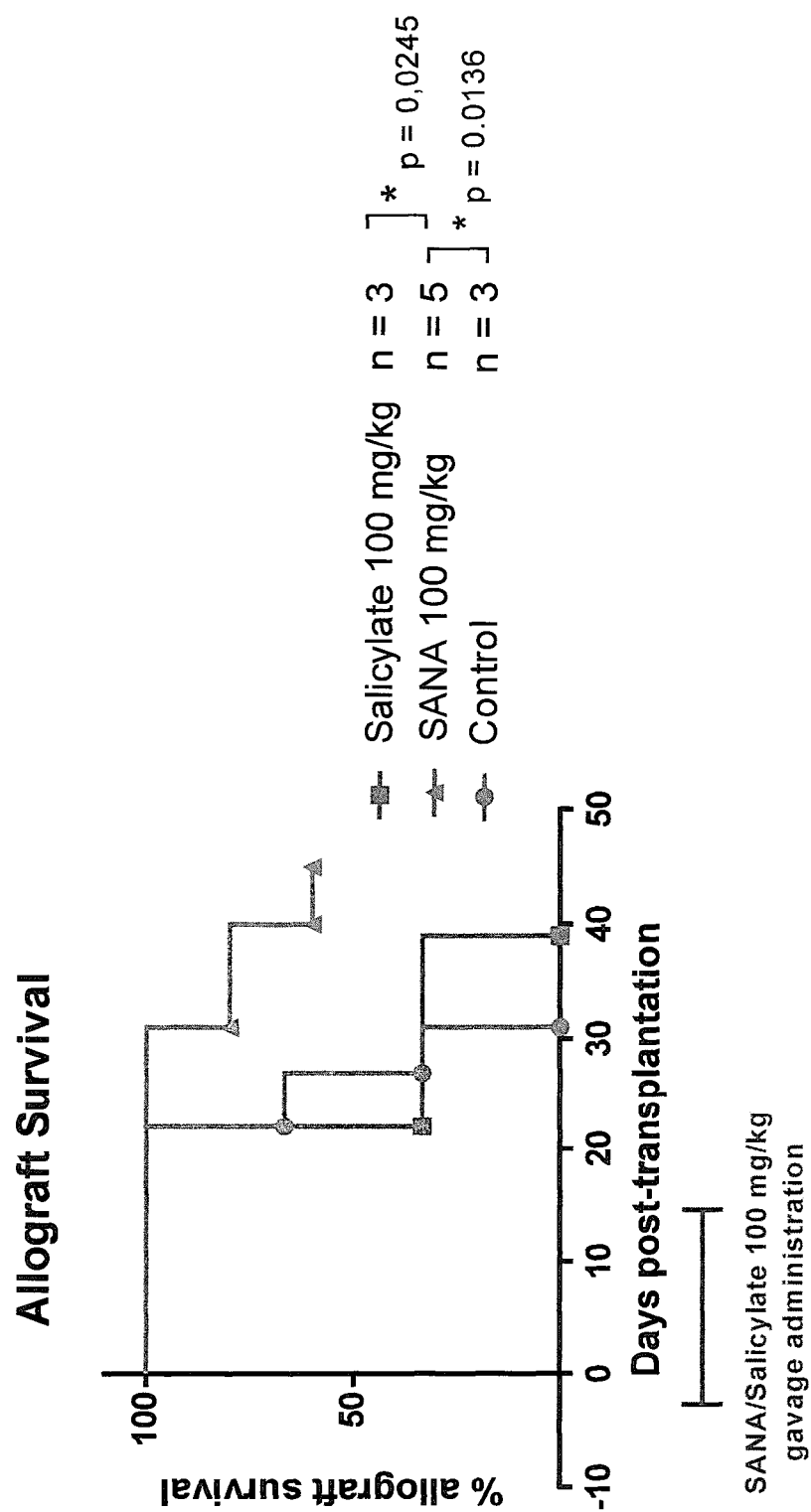
FIG. 17 illustrates that SANA treated skin allograft rejection better than salicylic acid.

Results from FIG. 17 indicate that treatment with SANA provided significant reduction in skin allograft rejection compared to salicylic acid. The study followed the protocol described above for FIG. 1, but further included a Salicylate group. C57BL/6 female mice were grafted with skin from the tails of C57BL/6 male mice. The skin graft is a small square (1 $cm^2$) and it was implanted onto the left subscapular region of the female mice. From one day before the transplantation until 15 days after it, the mice were treated daily with Salicylate (100 mg/kg, by oral gavage; Salicylate group), SANA (100 mg/kg, by oral gavage; SANA group) or vehicle (Control group). The vehicle used was a solution of Carboxy-Methyl-cellulose 0.5% m/v and Tween 80 0.5% v/v. At the end of the 15th day of administration, allografts were checked every 48/72 hours to assess the condition of the grafted skin. Rejection was diagnosed clinically when the allograft lost more than 50% of its size and/or more than 10%[1] of allograft was necrotic.

NON-PATENT CITATIONS

1. Manabe, I. "Chronic Inflammation Links Cardiovascular, Metabolic and Renal Diseases," Circ J. 75(12):2739-48 (2011).
2. Antman, E M et al. "Use of nonsteroidal antiinflammatory drugs: an update for clinicians: a scientific statement from the American Heart Association,"Circulation 115(12): 1634-42 (Mar. 27, 2007).

What is claimed is:

1. A method of treating a subject in need thereof comprising administering to said subject a therapeutically effective amount of a compound of Formula I:

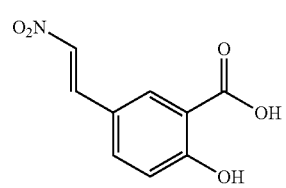

or a pharmaceutically acceptable salt thereof, wherein the subject in need thereof suffers from a condition selected from the group consisting of: chronic lung injury, Type-II diabetes, hypertension, obesity, and arthritis.

2. The method of claim 1, comprising administering the compound of Formula I with a pharmaceutically acceptable carrier.

3. The method of claim 2, wherein said subject is a mammal.

4. The method of claim 3, wherein said subject suffers from obesity.

5. The method of claim 4, wherein the administering prevents weight gain in said subject.

6. The method of claim 4, wherein the administering results in weight loss in said subject.

7. The method of claim 4, wherein the administering reduces insulin resistance in said subject.

8. The method of claim 4, wherein the administering reduces obesity-related diseases in said subject selected from the group consisting of: NASH, hypertension, and combinations thereof.

9. The method of claim 1, further comprising administering to the subject in need thereof a secondary therapeutic agent selected from the group consisting of: an anti-platelet agent, an inhibitor of angiotensin II, an ACE inhibitor, a $Ca^{++}$ channel blocker, an insulin sensitizer, a HMG-CoA reductase inhibitor, a beta blocker, a non-steroidal inflammatory drug, a steroidal anti-inflammatory drug, a peroxisome proliferator-activated receptors (PPAR) modulator, and combinations thereof.

10. A method of treating obesity in a subject in need thereof comprising administering to said subject a therapeutically effective amount of a compound of Formula I:

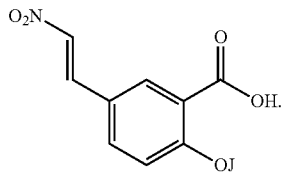

or a pharmaceutically acceptable salt thereof in combination with a pharmaceutically acceptable carrier.

11. The method of claim 10, wherein said subject is a mammal.

12. The method of claim 11, wherein the administering prevents weight gain in said subject.

13. The method of claim 11, wherein the administering results in weight loss in said subject.

14. The method of claim 11, wherein the administering reduces insulin resistance in said subject.

15. The method of claim 11, wherein the administering reduces obesity-related diseases in said subject selected from the group consisting of: NASH, hypertension, and combinations thereof.

16. The method of claim 11, further comprising administering to the subject in need thereof a secondary therapeutic agent selected from the group consisting of: an anti-platelet agent, an inhibitor of angiotensin II, an ACE inhibitor, a $Ca^{++}$ channel blocker, an insulin sensitizer, a HMG-CoA reductase inhibitor, a beta blocker, a non-steroidal inflammatory drug, a steroidal anti-inflammatory drug, a peroxisome proliferator-activated receptors (PPAR) modulator, and combinations thereof.

* * * * *

UNITED STATES PATENT AND TRADEMARK OFFICE
CERTIFICATE OF CORRECTION

PATENT NO. : 11,400,066 B2
APPLICATION NO. : 16/746035
DATED : August 2, 2022
INVENTOR(S) : Carlos Batthyány et al.

It is certified that error appears in the above-identified patent and that said Letters Patent is hereby corrected as shown below:

On the Title Page

In the first Column, in item (60) under "Related U.S. Application Data", Line 4, delete "provisional application No. 62/408,458" and insert --provisional application No. 62/408,459--

Signed and Sealed this
Eleventh Day of October, 2022

Katherine Kelly Vidal
*Director of the United States Patent and Trademark Office*